United States Patent [19]

Camus

[11] Patent Number: Plant 5,657

[45] Date of Patent: Feb. 4, 1986

[54] DIEFFENBACHIA CV. CAMRO

[76] Inventor: Robert Camus, Bouchemaine, Angers D111,49000, France

[21] Appl. No.: 517,218

[22] Filed: Jul. 25, 1983

[30] Foreign Application Priority Data

Jul. 26, 1982 [FR] France ..... 82-13150

[51] Int. Cl.[4] ..... A01H 5/00

[52] U.S. Cl. ..... Plt./88

[58] Field of Search ..... Plt./88

[56] References Cited

U.S. PATENT DOCUMENTS

P.P. 4,504 2/1980 Welker ..... Plt./88

*Primary Examiner*—Robert E. Bagwill

*Attorney, Agent, or Firm*—Synnestvedt & Lechner

[57] ABSTRACT

The application discloses a new asexually reproduced variety of Dieffenbachia cv. Camro wherein the chief characteristics are the large variegation on the surface of the leaves, a number of leaves per plant, and a lower proportion of shoots from the stool. The new variety is further characterized by a low sensitivity to the outside conditions and is also distinguishable by its pyramidal growth. The most advantageous applications of the invention bear on large scale ornamentation by means of very decorative Dieffenbachia.

7 Drawing Figures

1

The present invention relates to a new variety of Dieffenbachia cv. Camro distinguishable from the presently known varieties of this class and coloring by the following characteristics:

The particular arrangement of the variegation of the leaves. The variegations are arranged in the form of large, irregular white blotches or macules covering about 70% of the surface of the leaves in the summer and about 60% of the surface in the winter.

The new variety also shows this large variegation of the foliage in the juvenile stage as well as at the adult stage. The growth habit of the plant is pyramidal and compact.

The leaves or leaf blades of the new variety are longer and wider and its petioles are shorter than those of its male parent Compacta variety.

Because of the above-listed characteristics, the present invention provides the horticultural industry with an attractive, ornamental new variety of Dieffenbachia plants suitable for potting.

The goal of the applicant was to create a new variety which would have the desired characteristics, by systematic selection and crossings carried out by applicant.

The female stool (or root clump) was an unpatented and unnamed variety of Dieffenbachia selected from seedlings of a crossing of two other unpatented and unnamed varieties.

The male stool chosen came from an unpatented classic Compacta variety.

The hybridization operation used by the applicant is explained by the following schema:

Female: (Unpatented & unnamed variety) × (unpatented & unnamed variety).
Male: (Classic Compacta variety).

The seeds obtained from the offspring of this crossing therefore including a combination of the existing genetic factors present in the parent cells.

From the seeds of the crossing, applicant grew seedlings of 80 plants, each one distinct both physically and biologically.

The abnormal specimens and those which exhibited characteristics differing from those being sought after,

2 were discarded first. The remaining specimens were asexually reproduced by stool division and the resulting plants were evaluated against commercially grown varieties. The specimens were then selectively eliminated until a single specimen remained that possessed all of the desired characteristics.

This finally selected plant had leaves adorned with very pale yellow variegations on the young leaves and whiter ones on the adult leaves. These variegations occupy a much greater portion of the surface of the leaf, in the juvenile as well as at the adult stage, than with all other known Dieffenbachia varieties and particularly when compared with that of the Compacta type.

Among other distinguishing characteristics of the Camro variety are its pyramidal growth habit with small suckers or vegative shoots; its surface variegations or mottling is not appreciably affected by seasonal conditions, light or temperature, and the number of shoots comming from the base or stool is low and these shoots are of moderate height for this type of plant.

The applicant made numerous comparative studies between his newly created variety and the classic Compacta-type varieties. Significant differences were observed.

The new variety has leaves or leaf blades averaging about 25 cm. in length, i.e. about 5% longer than the length of the leaves of a classic Compacta variety.

The new variety has leaves averaging about 12 cm. in width, i.e. about 15% wider than those of the classic Compacta variety.

The length of the petioles of the new variety averaging about 14 cm., is about 13% shorter than the length of the petioles of a classic Compacta-type variety.

The number of leaves on the main stalk is about 11% greater than the number of leaves ordinarily borne on the main stalk of a classic Compacta-type variety.

The technical tests made on 500 plants verified that the characteristics and properties of the new variety hold true and are rigorously asexually transmissible, that is, by vegetative multiplication. This vegetative multiplication is performed by division of a shoot from the stool. The rooted shoot, when reaching moderate height, retains its pyramidal growth habit.

The above-mentioned shoots will be marketed under the varietal name Camro. It will be used on all commercial plants at the production stage as well as the marketing stage. It is thus that the new Camro variety of Dieffenbachia, object of the patent, is obtained. The botanical and descriptive characteristics are listed below are of a plant asexually reproduced by applicant in his greenhouse at Bouchemaine, Angers, France as observed by applicant in the summer of 1980.

DESCRIPTION

Classification: *Dieffenbachia compacta,* Family Araceae.
Plant: 40 to 60 cm. high.
Shoot:
*Young stalk color.*—Green and pale yellow.
Adult stalk color.—Green and white.
Leaf: About 24–26 cm in length, about 11–12 cm. in width and rougher in texture than the Compacta.
*Color of the young foliage.*—Front-green with wide, pale yellow variegations.
*Color of the adult foliage.*—Front-green with wide, white variegations. Back-dark green with wide, white variegations.
Petiole:
*On the adult plant.*—Petioles are about 13–15 cm. long and are striped alternatively with dark green veins and pale green veins. The inflorescence for the new variety has not been noted.
Development: Vigorous production of vegetation.

In this specification, color names beginning with a small letter signify the name of that color, as used in common speech is aptly descriptive.

IDENTIFICATION

To enable the identification of this variety of Dieffenbachia with large white variegations, some photographic reproductions in black and white and in color showing the distinctive elements of the plant accompany to the description to illustrate the new plant variety.

Photo 1 of Sheet 1 shows in color the initial stools. On the left, the known Compacta variety; on the right, the new variety.

Photo 2 of Sheet 1 shows in color the new variety at the juvenile stage; on the left, known Compacta-type variety at the same vegative stages.

Photo 3 on Sheet 1 shows, in color, the variegations of the backs of the leaves of adult plants. On the left, the classic, known, Compacta-type variety. On the right, the new variety.

Photo 4 on sheet 2 shows, in color, On the left, a specimen of the new variety at the adult stage. On the right, at the same vegatative stage, a classic Compacta-type variety.

Photo 5 on sheet 2 shows in color, a potted, adult Dieffenbachia cv. Camro plant.

Sheet 3 is a black and white illustration showing the variegations of leaves of the new Camro variety and the classic Compacta type.

The characteristically wavy leaf blades with undulating margins in the juvenile stages of the new Camro variety and their characteristically abundant white variegation, i.e., the well defined dark green mottling against a very pale yellow center field washed lightly with pale green (the center field covering about 70% of the leaf surface in the summer and about 60% of the leaf surface in the winter); and near-white midrib and secondary veins can be seen in Photo 2. As can be seen in Photos 1, 3, 4, and 5 the characteristic profuse variegation of the juvenile stage persists in the adult plants; however, with maturity the pale yellow background variegation becomes almost white. In addition, the leaves or leaf blades of the Camro variety are longer and wider than those of the male parent Compacta variety. Moreover, and as can be seen in Photo 3, the petioles are shorter than those of the Compacta variety.

I claim:

1. A new and distinct variety of Dieffenbachia plant substantially as described and shown, characterized by its compact pyramidal growth habit; its wavy leaf blades with undulating margins; its distinctly variegated leaf blades having well-defined, dark green mottling against a white center field washed lightly with pale green, the white center field covering about 70% of the leaf surface in the summer and about 60% of the leaf surface in the winter; and the distinctive leaf variegation persisting even as the leaves mature on the plant.

* * * * *

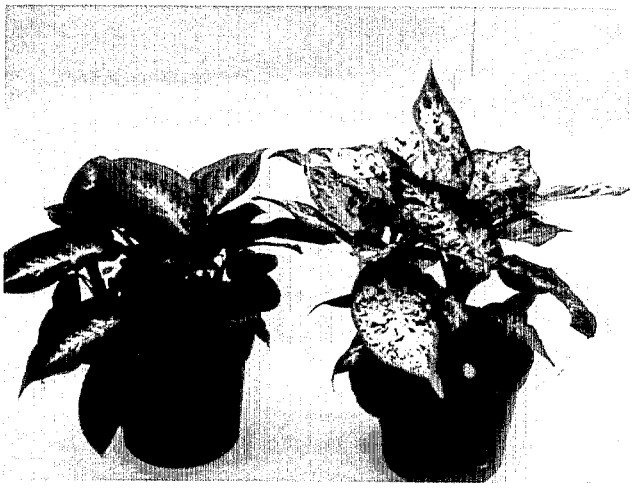
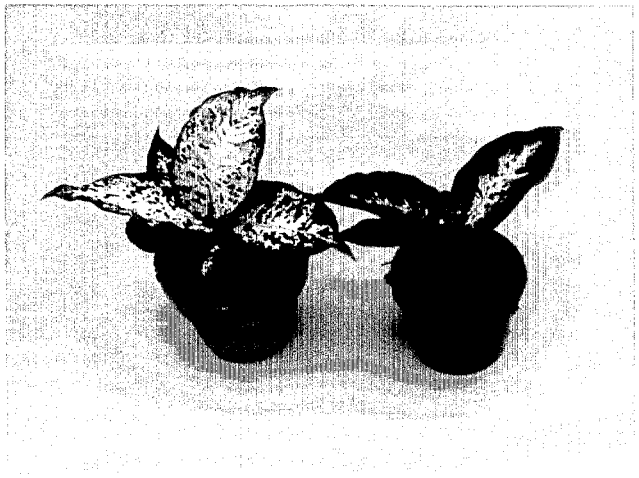
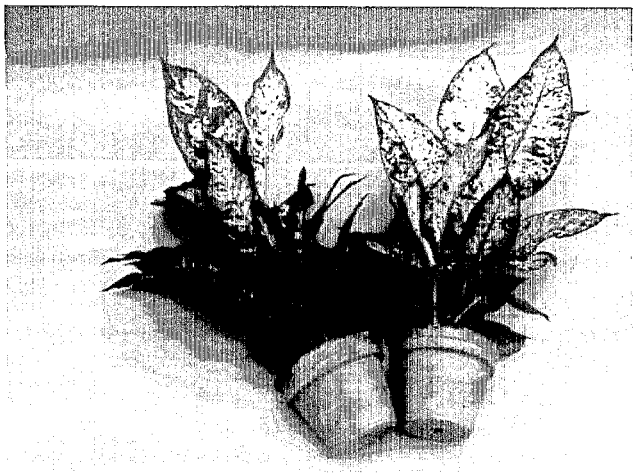

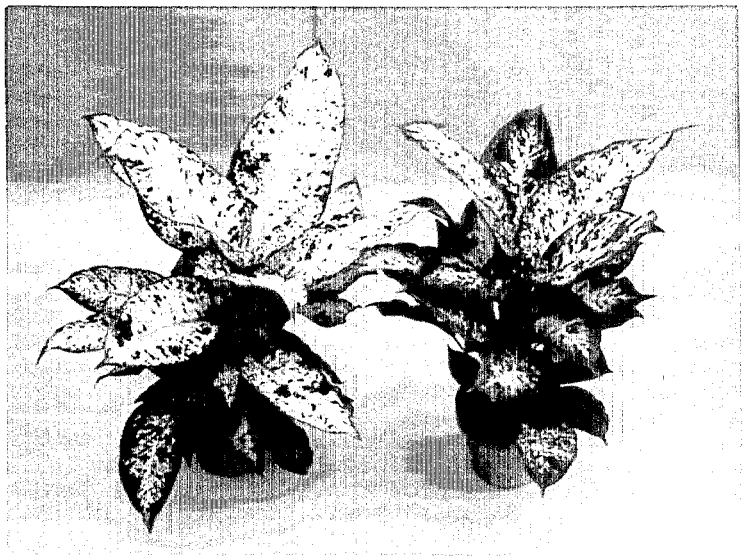
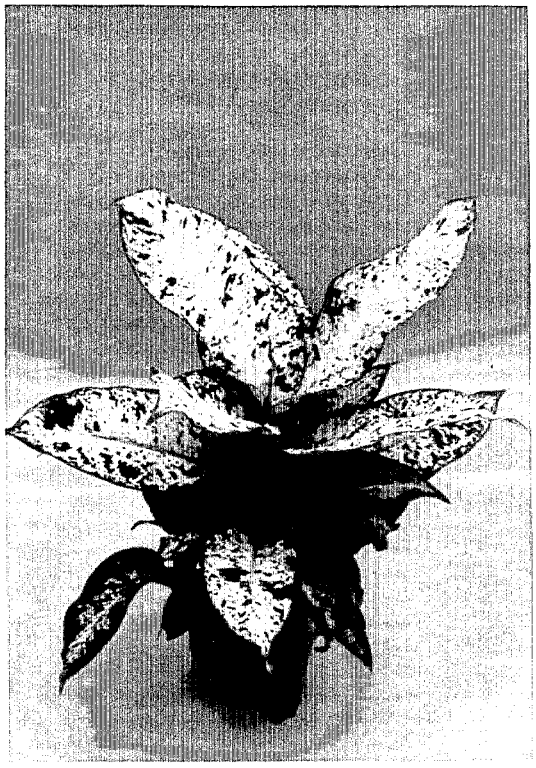

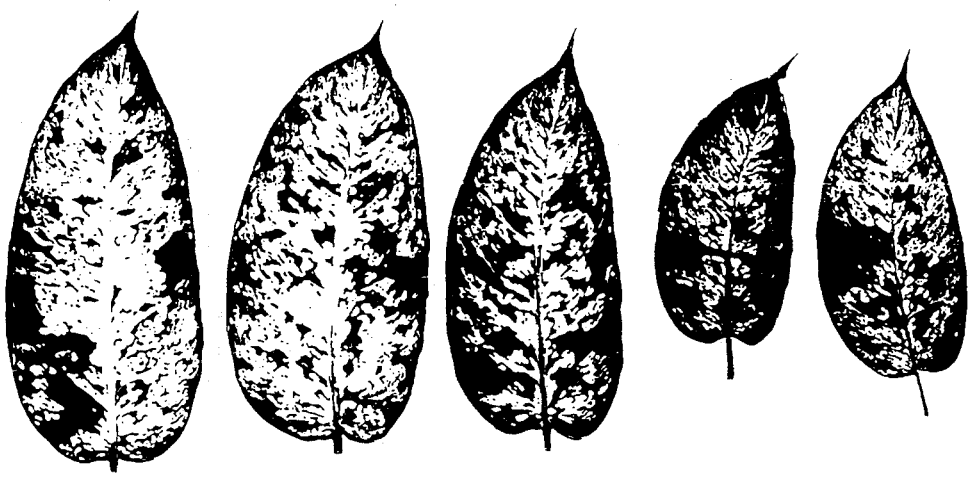
"COMPACTA"
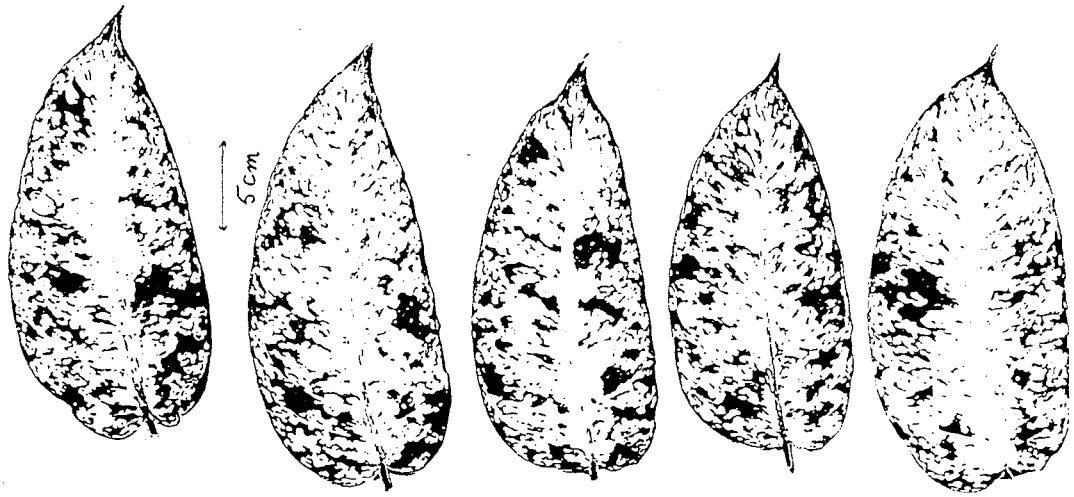
"CAMRO